United States Patent [19]

Recker et al.

[11] Patent Number: 5,002,530

[45] Date of Patent: Mar. 26, 1991

[54] CONTAINER FOR INFUSION SOLUTIONS

[75] Inventors: Antonius Recker, Glandorf; Manfred Rycyk, Bissendorf; Matthias Wesseler, Hilter, all of Fed. Rep. of Germany

[73] Assignee: Schiwa GmbH, Glandorf, Fed. Rep. of Germany

[21] Appl. No.: 314,136

[22] Filed: Feb. 23, 1989

[30] Foreign Application Priority Data

Feb. 25, 1988 [DE] Fed. Rep. of Germany ....... 8802443

[51] Int. Cl.[5] .............................................. A61M 37/00

[52] U.S. Cl. ......................................... 604/87; 604/82; 604/416; 206/219

[58] Field of Search ..................... 604/82, 87, 88, 408, 604/416, 82-92, 415, 411; 206/219-222

[56] References Cited

U.S. PATENT DOCUMENTS

| | | | |
|---|---|---|---|
| 2,353,153 | 8/1942 | Ferrel | 604/82 |
| 2,580,836 | 1/1952 | Rausch | 604/416 |
| 3,001,525 | 9/1961 | Hendricks | 604/416 |
| 4,396,383 | 8/1983 | Hart | 604/82 |
| 4,403,992 | 9/1983 | Bertellini et al. | 604/82 |
| 4,467,588 | 8/1984 | Carveth | 604/87 |
| 4,583,971 | 4/1986 | Bocquet et al. | 604/88 |
| 4,645,073 | 2/1987 | Homan | 604/88 |
| 4,838,875 | 6/1989 | Somor | 604/247 |
| 4,911,692 | 3/1990 | Martin | 604/416 |

*Primary Examiner*—Stephen C. Pellegrino
*Assistant Examiner*—Kathleen A. Daley
*Attorney, Agent, or Firm*—Oblon, Spivak, McClelland, Maier & Neustadt

[57] ABSTRACT

The container is intended for mixing infusion solutions with ingredients and for administering the mixture. It consists of a bag which forms the mixing space, is made of flexible material and is provided on each of the two narrow sides with a tubular connecting part, the connecting parts being equipped with connectors.

8 Claims, 1 Drawing Sheet

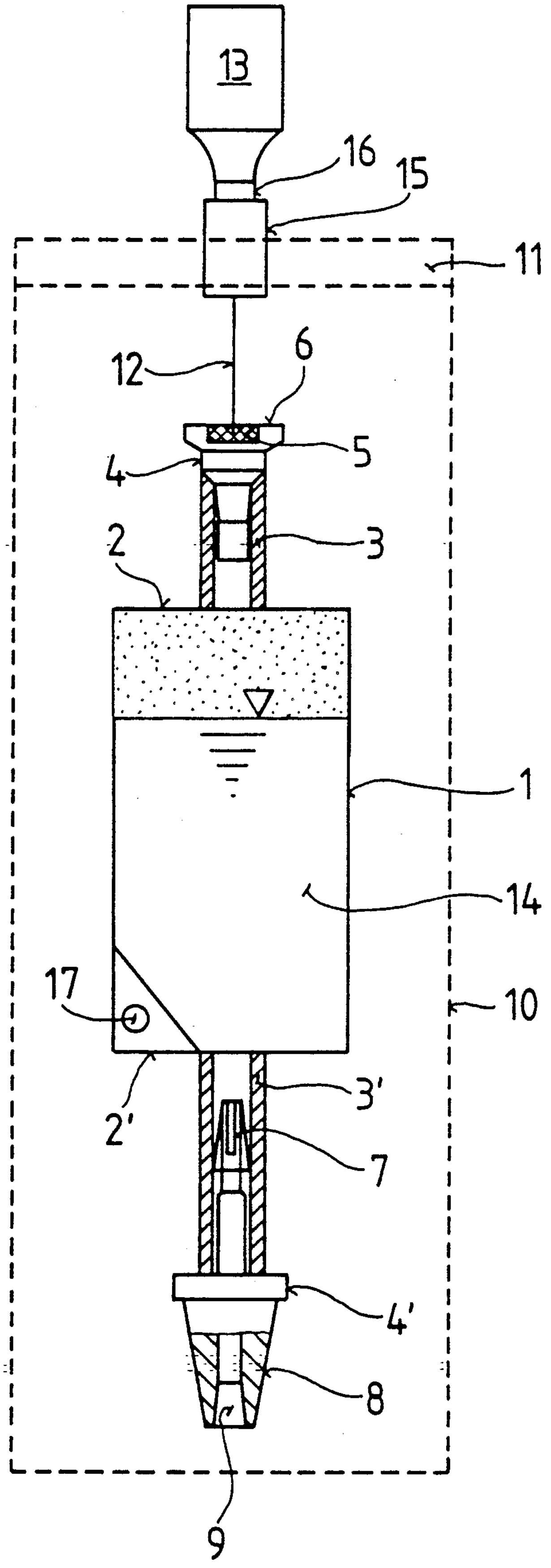
13
16
15
11
12
6
5
4
3
2
1
14
17
10
2'
3'
7
4'
8
9

CONTAINER FOR INFUSION SOLUTIONS

BACKGROUND OF THE INVENTION

The present invention relates to a container for infusion solutions for mixing the solution with solid and/or liquid ingredients and for administering the mixture.

Mixing an infusion solution with ingredients has been carried out to date by a procedure in which, for example, physiological saline solution was removed from a glass vial by means of a syringe with an attached disposable needle and introduced into a container with dry substance. The medium mixed therein was then transferred to the patient by means of an infusion apparatus.

The disadvantages are that, on the one hand, this method is very tedious since it is necessary to ensure that, when the liquid medium is added to the container holding the dry substance, no excess pressure is generated, and, on the other hand, when the needle is removed from the stopper of the container aerosols may be formed. When highly toxic substances, for example cytostatics, are being handled, contamination leads to dangerous diseases.

SUMMARY OF THE INVENTION

It is an object of the present invention to provide a container for infusion solutions which both permits an infusion solution to be mixed with ingredients with little contamination and furthermore allows the mixture to be administered.

We have found that this object is achieved if the container consists of a bag which forms a mixing space, is made of flexible material and is provided on each of the two narrow sides with a tubular connecting part, the connecting parts being equipped with connectors.

BRIEF DESCRIPTION OF THE DRAWINGS

Details of the novel container and further embodiments are described with reference to the drawing illustrating an embodiment.

DESCRIPTION OF THE PREFERRED EMBODIMENT

The container consists of a bag 1 which forms a mixing space and is made of a film material, for example PVC or another thermoplastic elastomer, and is welded or adhesively bonded on each of the two narrow bag sides 2, 2' to a connecting tube 3, 3' of similar material. A connector 4, 4' is inserted into each of the free tube ends, the connector being held firmly by virtue of an external diameter which is slightly larger than the internal diameter of the tube. The connector 4 on the inlet side is closed by means of a rubber stopper 5, flush with the end section 6 of the connector, so that the connector end can be disinfected in a simple manner.

The connector 4' on the outlet side is equipped with a cut-off valve 7 and its connecting end 8 is conical and is provided with a Luer inner cone 9. However, this connector can be identical to the connector 4 on the inlet side.

To keep the container sterile, the bag 1 together with the connecting tubes 3, 3' and the connectors 4, 4' is welded into a sterilizable surrounding bag 10, which advantageously has a tear strip 11.

To use the novel container, the solid and/or liquid ingredients to be admixed are first passed from a stock vessel 13 by means of a hollow needle 12 penetrating the stopper 5 into the bag 1, which is partially full of the infusion solution 14. The needle is part of an adapter 15 which has a connection 16 for the stock vessel 13. After the ingredients have been passed in, the substances are mixed by shaking the bag.

In another embodiment of the container according to the invention, the stock vessel 13 is at the same time the mixing container into which the infusion solution is transferred via the needle 12 of the adapter 15 by means of pressure on the bag 1. When mixing in the mixing container is complete, the mixed solution is returned to the bag with the aid of the reduced pressure generated in the bag.

After connection of an administration tube, for example a catheter, to the connector 4' on the outlet side, the cut-off valve 7 can be opened in order to administer the solution present in the bag.

When a transfusion apparatus, for example an infusion apparatus, is used, the bag can be fastened to an appropriate hook or stand by means of a suspending eye 17 in the bag 1, to permit better administration of the medium.

We claim:

1. A container for mixing infusion solutions with solid and/or liquid ingredients and for administering the mixture, comprising:
   a bag which defines a mixing space, said bag being made of a flexible material and having two narrow sides at each of its ends, said two narrow sides defining inlet and outlet sides, each narrow side of said bag being provided with tubular connecting parts, said tubular connecting parts being equipped with connectors, said container defining a sterilizable surrounding bag which surrounds said bag, wherein said tubular connecting parts and said connectors are located completely within said surrounding bag, said container further comprising an adapter and needle arrangement, said adapter and needle arrangement extending from an edge portion of said surrounding bag to one of said connectors, said needle extending within said container to said connector to allow fluid communication between said connector and said adapter, said adapter being adapted for receiving a vessel containing said solid and/or liquid ingredient, whereby said vessel is located on the exterior of said surrounding bag when said vessel is connected to said adapter.

2. A container as claimed in claim 1, wherein the connecting part on the inlet side is closed with a connector which receives a rubber stopper.

3. A container as claimed in claim 1, wherein the connecting part on the outlet side is closed with a connector having a cut-off valve.

4. A container as claimed in claim 1, wherein the connector on the outlet side is conical at its 5. A container as claimed in claim 1, wherein the connector on the outlet side has a Luer inner cone.

6. A container as claimed in claim 1 wherein said sterilizable surrounding bag has a tear strip at said edge portion.

7. A container as claimed in claim 1, wherein the bag is coordinated with a further mixing bag which can be connected by means of said adapter to the connector on the inlet side.

8. A container as claimed in claim 1, wherein a suspending eye is arranged in the bag in order to infuse the mixture by means of a transfusion apparatus.

* * * * *